US008093004B2

(12) United States Patent
Kukreti et al.

(10) Patent No.: US 8,093,004 B2
(45) Date of Patent: Jan. 10, 2012

(54) METHOD OF DETECTING AND PREDICTING BRONCHODILATORY RESPONSE TO BETA AGONIST

(75) Inventors: Ritushree Kukreti, Delhi (IN); Pallav Bhatnagar, Mumbai (IN); Chandrika Rao, New Delhi (IN); Balram Ghosh, New Delhi (IN); Samir Kumar Brahmachari, New Delhi (IN); Randeep Guleria, New Delhi (IN); Chinmoyee Das, New Delhi (IN)

(73) Assignees: Council of Scientific & Industrial Research, New Delhi (IN); Piramal Life Sciences Limited, Mumbai (IN)

( * ) Notice: Subject to any disclaimer, the term of this patent is extended or adjusted under 35 U.S.C. 154(b) by 548 days.

(21) Appl. No.: 10/833,270

(22) Filed: Apr. 28, 2004

(65) Prior Publication Data

US 2005/0255479 A1    Nov. 17, 2005

(51) Int. Cl.
C12Q 1/68 (2006.01)
C12P 19/34 (2006.01)
C07H 21/02 (2006.01)
C07H 21/04 (2006.01)

(52) U.S. Cl. ...... 435/6.17; 435/6.1; 435/6.11; 435/6.12; 435/91.2; 536/24.31; 536/24.33

(58) Field of Classification Search .................. None
See application file for complete search history.

(56) References Cited

U.S. PATENT DOCUMENTS

| | | | | |
|---|---|---|---|---|
| 5,541,308 | A * | 7/1996 | Hogan et al. | 536/23.1 |
| 6,156,503 | A * | 12/2000 | Drazen et al. | 435/6 |
| 6,498,009 | B1 | 12/2002 | Liggett | |
| 6,586,183 | B2 * | 7/2003 | Drysdale et al. | 435/6 |
| 2002/0032319 | A1 * | 3/2002 | Cargill et al. | 536/23.1 |
| 2004/0171056 | A1 * | 9/2004 | Stanton, Jr. | 435/6 |

OTHER PUBLICATIONS

Israel et al., Oct. 2004, Lancet 364: 1505-1512.*
Taylor et al., 2005, Am J. Repir Crit. Care Med 172: 700-703.*
Choudhry et al., 2005, Am. J. Respir. Crit. Care Med 171: 563-570.*
Hirschhorn et al., 2002, Genetics in Medicine. 4: 45-61.*
Araki et al., 2003, J Am Soc. Nephrol. 14: 2015-2024.*
Buck et al. Biotechniques, 1999, 27:528-536.*
Chiou et al., 2002, BioTechniques, 33: 557-564.*
GenBank, Accession No. M15169.*
Evans et al. Drug Metabolism and Disposition. 2001. 29: 606-610.*
Brown et al. Clinical Chemistry. 2001. 47: 2053-2055.*
Schering-Plough package insert for Proventil® HFA , Nov. 2007, available at url: <proventilhfa.com/phfa/application>.*
Lima et al. Clinical Pharmacol Ther. 1999. 65: 519-525.*
Bjermer, L. et al., (2002), "The use of leukotriene receptor antagonists (LTRAs) as complementary therapy in asthma", *Monaldi Arch Chest Dis*, vol. 57, No. 1, pp. 76-83. (Abstract submitted).
Clark, A., (1990), "Inference of Haplotypes from PCR-amplified Samples of Diploid Populations", *Mol. Biol. Evol.*, vol. 7, No. 2, pp. 111-122.
Cockcroft, D. W. et al., (1996), "Functional antagonism: tolerance produced by inhaled $\beta_2$ agonists", *Thorax*, vol. 51, pp. 1051-1056.
Dennis, S. et al., (2000), "Regular inhaled salbutamol and asthma control: the TRUST randomised trial", *The Lancet*, vol. 355, pp. 1675-1679.
Dewar, C. et al.,(1998), "$\beta_2$-adrenoceptor polymorphisms are in linkage disequilibrium, but are not associated with asthma in an adult population", *Clinical and Experimental Allergy*, vol. 28, pp. 442-448.
Dewar, J. et al., (1997), "The glutamine 27 $\beta_2$-adrenoceptor polymorphism is associated with elevated IgE levels in asthmatic families", *Journal of Allergy and Clinical Immunology*, vol. 100, No. 2, pp. 261-265.
Drazen, J. et al., (2000) "Heterogeneity of therapeutic responses in asthma", *British Medical Bulletin*, vol. 56, No. 4, pp. 1054-1070.
Eh, W. et al., (2003) "Inhaled long acting beta agonists for stable chronic asthma", *Cochrane Database Syst Rev*, vol. 4. (Abstract submitted).
Green, S. et al., (1994), "Amino-Terminal Polymorphisms of the Human $\beta_2$-Adrenergic Receptor Impart Distinct Agonist-Promoted Regulatory Properties", *Biochemistry*, vol. 33, No. 32, pp. 9414-9419.
Green, SA. et al., (1995), "Influence of beta 2-adrenergic receptor genotypes on signal transduction in human airway smooth muscle cells", *Am J. Respir. Cell Mol. Biol.*, vol. 13, No. 1, pp. 25-33. (Abstract submitted).
Hoit, B. et al., (2000), "$\beta_2$-Adrenergic receptor polymorphisms at amino acid 16 differentially influence agonist-stimulated blood pressure and peripheral blood flow in normal individuals", *American Heart Journal*, vol. 139, No. 3, pp. 537-542.
Johnson, M., (1998), "The $\beta$-Adrenoceptor", *American Journal Respiratory and Critical Care Medicine*, vol. 158, pp. S146-S153.
Kobilka, B. et al., (1987), "cDNA for the human $\beta_2$-adrenergic receptor: A protein with multiple membrane-spanning domains and encoded by a gene whose chromosomal location is shared with that of the receptor for platelet-derived growth factor", *Proc. Natl. Acad. Sci.* vol. 84, pp. 46-50.
Large, V., (1997), "Human Beta-2 Adrenoceptor Gene Polymorphisms Are Highly Frequent in Obesity and Associate with Altered Adipocyte Beta-2 Adrenoceptor Function", *J. Clin Invest.*, vol. 100, No. 12, pp. 3005-3013.
Liggett, S. et al., (1998), The Ile164 $\beta_2$-Adrenergic Receptor Polymorphism Adversely Affects the Outcome of Congestive Heart Failure, *J. Clin Invest*, vol. 102, No. 8, pp. 1534-1539.
Lipworth, BJ. et al., (1999), "Beta2-adrenoceptor polymorphism and bronchoprotective sensitivity with regular short- and long-acting beta2-agonist therapy", *Clinical Science*, vol. 96, No. 3, pp. 253-259. (Abstract Submitted).
Martin, R., (2003), "Considering therapeutic options in the real world", *J. Allergy Clin Immunol*, vol. 112, No. 5, pp. S112-S115.

(Continued)

Primary Examiner — Carla Myers
(74) Attorney, Agent, or Firm — Foley & Lardner LLP

(57) ABSTRACT

Present invention relates to a method for predicting an individual's bronchodilatory response to a $\beta$ agonist. Present invention particularly relates to the detection of specific allelic variants of the $\beta$2AR gene and their use as pharmacogenetic markers towards response to $\beta$ agonist.

6 Claims, 8 Drawing Sheets

OTHER PUBLICATIONS

Figure 1A:
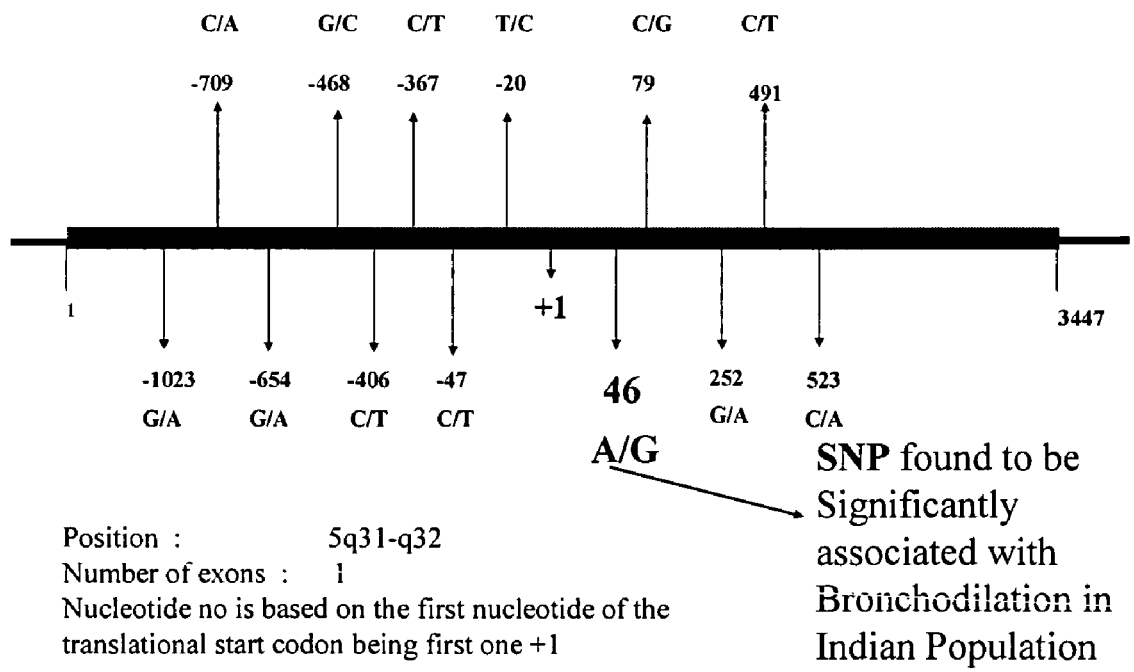

Martinez, F., (1997), "Association between Genetic Polymorphisms of the $\beta_2$-Adrenoceptor and Response to Albuterol in Children with and without a History of Wheezing", *J. Clin. Invest.*, vol. 100, No. 12, pp. 3184-3188.

O'Connor, B. et al., (1992), "Tolerance to the nonbronchodilator effects of inhaled beta 2-agonists in asthma", *The New England Journal of Medicine*, vol. 327, No. 17, pp. 1204-1208.

Ohe, M., et al., (1995), Beta$_2$ adrenergic receptor gene restriction fragment length polymorphism and bronchial asthma, *Thorax*, vol. 50, pp. 353-359.

Reihsaus, E. et al., (1993), "Mutations in the gene encoding for the beta 2-adrenergic receptor in normal and asthmatic subjects", *Am J. Respir Cell Mol Biol.*, vol. 8, No. 3, pp. 334-339. (Abstract submitted).

Sakane, N. , (1999)m "$\beta_2$-adrenoceptor gene polymorphism and obesity", *The Lancet*, vol. 353, p. 9168.

Scott, M. et al., (1999), "Identification of novel polymorphisms within the promoter region of the human $\beta_2$ adrenergic receptor gene", *British Journal of Pharmacology*, vol. 126, pp. 841-844.

Settipane, R. A., (2003), "Defining the Effects of an Inhaled Corticosteroid and Long-Acting β-Agonist on Therapeutic Targets", *Allergy and Asthma Proc.* vol. 24, No. 2, pp. 85-89.

Suki, B. et al., (2003), "Temporal dynamics of recurrent airway symptoms and cellular random walk", *J. Appl. Physiol*, vol. 95, No. 5, pp. 2122-2127.

Tan, S. et al., (1997), "Association between $\beta_2$ adrenoceptor polymorphism and susceptibility to bronchodilator desensitisation in moderately severe stable asthmatics", *The Lancet*, vol. 350, pp. 995-999.

Turki, J. et al.,(1996), "Myocardial signaling defects and impaired cardiac function of a human $\beta_2$-adrenergic receptor polymorphism expressed in transgenic mice", *Proc. Natl. Acad. Sci*, vol. 93, pp. 10483-10488.

Xu, B. et al., (2000), "$\beta_2$-adrenergic receptor gene polymorphisms in myasthenia gravis (MG)", *Clinical & Experimental Immunology*, vol. 119, pp. 156-160.

Ahern, H. "Biochemical, Reagent Kits Offer Scientists Good Return on Investment" The Scientist, Jul. 1995, vol. 9, No. 15, pp. 20-25.

US Office Action in U.S. Appl. No. 12/230,913 dated Jun. 29, 2010.

Mitsuhashi, M. "Technical Report: Part 2. Basic Requirements for Designing Optimal PCR Primers" Journal of Clinical Laboratory Analysis, 1996, vol. 10, pp. 285-293.

* cited by examiner

Good Responders (56 Patients)

(Asthmatics)     AA    AG    GG 5    33    18

8.9%    58.9%    32.1%

Poor Responders (67 Patients)

(Asthmatics)     AA    AG    GG 16    44    7

23.8%    65.6%    10.4%

Normal Individuals (20 people)    AA    AG    GG (Non-Asthmatics)    5    10    5

25%    50%    25%

Fig. 1d

METHOD OF DETECTING AND PREDICTING BRONCHODILATORY RESPONSE TO BETA AGONIST

FIELD OF THE INVENTION

Present invention relates to a method for predicting an individual's bronchodilatory response to a β-agonist. Present invention particularly relates to the detection of specific allelic variants of the β2AR gene and their use as pharmacogenetic markers towards response to β agonist.

BACKGROUND INFORMATION

Asthma is a chronic inflammatory disease of the airways characterized by recurrent episodes of wheezing, chest tightness and coughing, which vary in severity and frequency from person to person (Suki et al., 2003). It is a condition in which the airways of the lungs become either narrowed or completely blocked, impeding normal breathing. However in asthma this obstruction of the lungs is reversible, either spontaneously or with medication. Currently three main asthma treatments are available (Jeffrey et al., 2000): (a) Inhaled glucosteroids (Martin, 2003; Settipane et al., 2003) (b) beta 2-agonists (Eh et al., 2003) and (c) leukotriene inhibitors (Bjermer et al., 2002). In the patients suffering from asthma with an apparently identical phenotype, response to drug treatment may be remarkably variable (Drysdale et al., 2000). β2AR agonists are recommended for first-line use as bronchodilator therapy in asthma (National Asthma Education and Prevention Program (1997) Expert Panel Report II). Short and long acting β 2 agonists exhibit protective effects against a variety of direct and indirect bronchoconstrictor stimuli (Cockcroft et al., 1996). The beta-adrenergic receptor has been subdivided into at least three distinct groups: β1, β2, β3 classically identified in cardiac, airway smooth muscle, and adipose tissue, respectively (Johnson M, 1998). There is a 65-70% homology between β1, β2 and β3 receptors. There is now good evidence that beta adrenoreceptors exist in activated and inactivated forms and under resting conditions these two forms are in equilibrium with the inactivated state being predominant (Johnson M, 1998). The β2AR is in the activated form when it is associated with the a subunit of the G protein, together with a molecule of guanosine triphosphate (GTP), and it is through this a subunit that the receptor is coupled to adenylate cyclase. The replacement of the GTP by GDP catalyzes the conversion of ATP to cAMP by the enzyme and dramatically reduces the affinity of the a subunit for the receptor, causing dissociation and the receptor to return to its low-energy, inactivated form (Johnson M, 1998). The β2 adrenergic receptor is the key target for the β2 agonist drugs used for bronchodilation in asthma. The β2AR is a G protein-coupled, and has an extracellular amino terminus, seven transmembrane spanning domain, three intracellular and three extracellular loops, and an intracellular carboxyl terminus, that is widely distributed throughout the body especially in smooth muscle cells of bronchi, and mediates the action of catecholamines in various tissues and organs. The β2AR is composed of 413 amino acid residues of approximately 46,500 Dalton (Da) (Drysdale et al., 2000). The β2 A R is encoded by an intronless gene on chromosome 5q31-32 (Kobilka et al., 1987). Johnson M., (1998) have reported several single nucleotide polymorphisms (SNPS) in the coding block of the β2AR gene that lead to significant genetic variability in the structure of the β2 AR protein in the human population (GenBank Accession Numbers AF022953.1 GI:2570526; AF022954.1 GI:2570528; and AF022956.1 GI:2570532).

These SNPs are located at nucleotides 46 (A or G), 79 (C or G), and 491 (C or T) of the β2 AR coding sequence, and result in variation that occurs in the amino-terminus of the receptor at amino acids 16 (Arg or Gly) and 27 (Gln or Glu) and in the fourth transmembrane spanning domain at amino acid 164 (Thr or Ile), respectively. These amino acid variants have clear phenotypic differences as demonstrated by recombinant cell studies (Green et al., 1994), primary cultures of cells (CHW-1102) endogenously expressing these variants (Green et al., 1995), and transgenic mice overexpressing the Thr164 or Ile164 receptors in the heart (Turki et al., 1996). Besides, a synonymous polymorphism of C or A at nucleotide 523 in the coding sequence has been reported to be associated with altered responsiveness to salbutamol in Japanese families (Ohe et al., 1995). In addition to the above polymorphisms in the coding block, several SNPs in the 5' promoter region have recently been identified and are located at nucleotides −1023 (A or G), −654 (G or A), −468 (C or G), −367 (T or C), −47 (C or T) and −20 (T or C) (Scott et al., 1999). Recently two more SNPs at −709(C or A) and −406(C or T) are reported by Drysdale et al (2000). Thus, thirteen polymorphic sites have previously been identified in the region of the β2AR gene located between nucleotides 565 and 2110 of GenBank Accession No. M15169.1. Different groups have suggested associations between some of the above β2AR amino acid variants and increased susceptibility to various conditions, including: high blood pressure (Gly16 variant, Hoit et al., 2000); atopy (Gly16 variant, Dewar et al., 1998); nocturnal asthma (Gly16 variant, Turki et al., 1995); response to treatment for obesity (Gly16 variant, Sakane et al., 1999); myasthenia gravis (Arg16 variant, Xu et al., 2000); childhood asthma (Gln27 variant, Dewar et al., 1997); obesity (Glu27 variant, Large et al., 1997); and mortality from congestive heart failure (Ile164 variant, Liggett et al., 1998).

It has also been suggested that some of the β2AR gene polymorphisms discussed above may act as disease modifiers in asthma or may be the basis for the known interindividual variation in the bronchodilating response to β agonists (Drysdale et al., 2000). Indeed, Martinez et al (1997) have reported that individuals homozygous or heterozygous for the Arg16 variant are more likely to respond to albuterol than individuals homozygous for the Gly16 variant. Interestingly, another group has reported bronchodilator desensitization in asthmatics homozygous for the Gly16 variant following continuous therapy with the beta-agonist formoterol (Tan et al., 1997). At the same time, however other studies failed to demonstrate any correlations between adverse drug response and regular treatment with beta-agonists (Lipworth et al., 1999).

Asthma is one of the most common diseases worldwide. There are 15-20 million asthmatics in India and 6% of the children in India suffer from asthma (Chabra S. K., 1998). Asthma is a complex, multifactorial disorder, involving many genes as well as some environmental factors (Suki et al., 2003). Genetic factors have yet to be fully elucidated for the Indian population. A lot of irrational drug prescription occurs due to lack of knowledge of the individual and inter-racial variations in the drug response to most of the currently prescribed drugs for asthma leading to wrong treatment. This could prove to be fatal in certain acute cases. These situations can be avoided using prior knowledge of the individual's response to the drug prescribed based on pharmacogenomic rationale. There are also varied side effects due to irrational drug prescription like tremor, palpitation, trachycardia and tolerance to the efficacy (O'Connor et al., 1992, Dennis et al., 2000). The allelic variants of β2AR gene at nucleotide position 46 (A/G), disclosed in the present invention, have been found to be the dictator marker for the bronchodilatory response of the beta agonist drugs particularly in the Indian population. It has been observed that sometimes the patients suffering from asthma do not respond to salbutamol, and it takes long time (days to months) to identify that a particular patient is not responding to the medication. During this time it is very difficult to provide symptomatic relief for the patient. If the physician can identify the responders or the non-responders at the beginning of the treatment, the dose titration time will be saved and the patient would get timely treatment with other alternative therapeutics. In case of an emergency, correct and timely treatment can be given to the non-responders, which may be life-saving.

Drysdale et al (2000) in the US patent application no. 811286 have disclosed a method wherein three SNPs at positions −654 (G/A), 46 (A/G) and 252 (G/A) of the β2AR gene determine the response of beta agonist drugs in the Caucasian population. The method and diagnostic kit claimed by Drysdale et al (2000) is more time consuming, expensive (due to use of three sets of probes and primers and related fine biochemicals). Further their method is restricted for use to the Caucasian population. Hence a need exists to develop an inexpensive, rapid and specific diagnostic method and kit for screening the Indian population for drug response to beta agonists as there are 15-20 million asthmatics in India and 6% of the children in India suffer from asthma. The SNP disclosed in the invention has been found to be associated with the biologic and therapeutic phenotype and has a strong predictive power as an indicator of drug response of individual patient.

Asthma is a complex disease with a phenotype that has been clinically difficult to define. Inhaled beta-adrenergic agonists are the most commonly used medications for treatment of asthma. Polymorphisms of the β2AR can affect regulation of the receptor. The novelty of the present invention is in providing strong association of one single nucleotide polymorphism as pharmacogenetic locus determining the drug response towards beta agonists in Indian asthmatics. The novelty of the present invention is in providing a method for prediction of bronchodilatory response by detecting allelic variants of β2AR gene at position 46 (A/G). This single nucleotide polymorphism has been found to be solely associated with the drug response in the Indian asthmatics. Moreover, this SNP has been found to be a dictator marker for the drug response in the Indian population. Drysdale et al., found three SNPs together contributing the drug response in the Caucasian population whereas in Indian population these three SNPs are found to be unlinked and therefore we observed that taking these three SNPs together in Indian population is less significant than one SNP (A→G).

The invention also provides specific novel probes and primers and diagnostic kit for screening the Indian population for responders to the β2 agonist.

The invention further provides a cheaper and faster method for predicting drug response of the Indian asthmatics to β2 agonist. This polymorphism in β2AR gene has great commercial value both as a cheaper diagnostic reagent and for developing new treatments for this disease.

OBJECTS OF THE INVENTION

Main object of the invention is to provide a method for detecting and predicting bronchodilatory response to a β2 agonist.

Another object of the present invention provides a method of detecting and predicting specific allelic variants or single nucleotide polymorphisms of β2AR gene.

Yet another object of the present invention relates to the method of preparing pharmacogenetic markers for detecting and predicting bronchodilatory response to β2 agonist.

Still another object of the invention is to provide a diagnostic kit for detecting and predicting bronchodilatory response to a β2 agonist asthmatics.

Still another object of the present invention provides novel phramcogenetic markers for detecting and predicting bronchodilatory response to β2 agonist Another object is to provide a faster and specific method for screening asthmatics for responders and non-responders to β2 agonist.

Yet another object of the invention is to provide the genotype of the pharmacogenetic locus in β2A R gene for predicting the drug response.

Yet another object of the invention is to provide novel and specific probes and primers for detecting nonsynonymous allelic variants (A/G) of β2AR gene at nucleotide position 46 in the coding region, useful for screening the Indian asthmatic population for the drug response.

Yet another object of the invention is to study association of polymorphisms in β2AR gene with asthma.

BRIEF DESCRIPTIONS OF THE ACCOMPNAYING DRAWINGS/FIGURES

FIG. 1a: Schematic representation of all the SNPs including nonsynonymous polymorphism in β2AR gene.

Figure 1B:
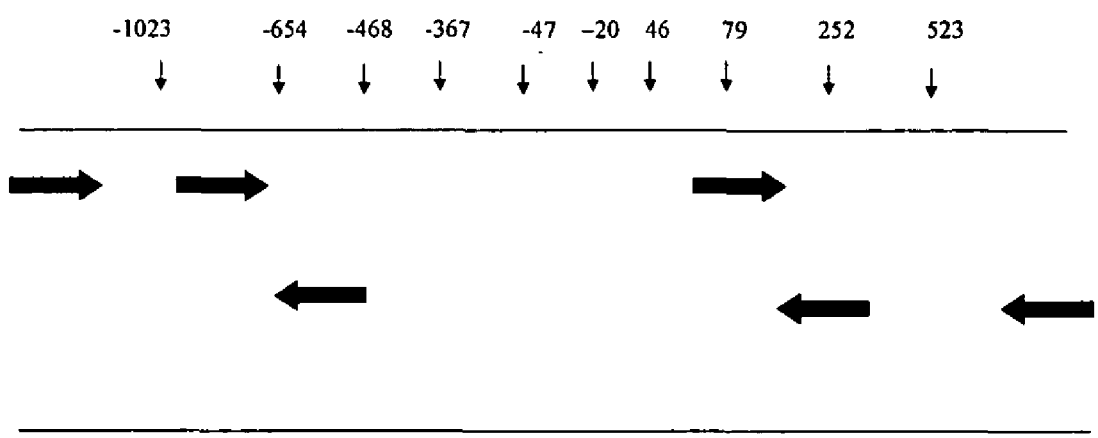

FIG. 1b Primers having SEQ. ID Nos. 2 and 3 for PCR amplification of the region covering the full β2AR gene.

Figure 1C:
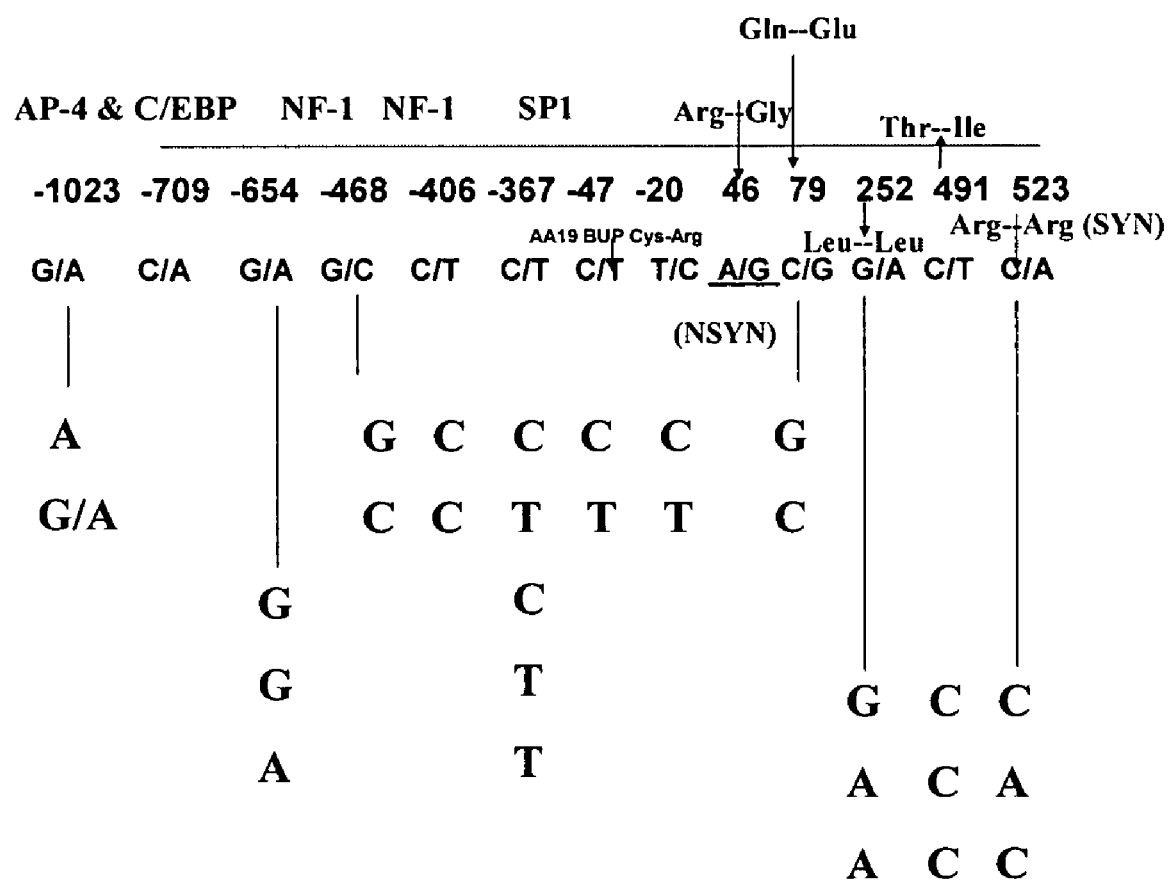

FIG. 1c Localization of SNPs and the identification of linkage disequilibrium of the regions of the β2AR gene in the Indian Population.

FIG. 1d Showing distribution of A/G polymorphism (genotype) at 46 nucleotide position.

Figure 2A:
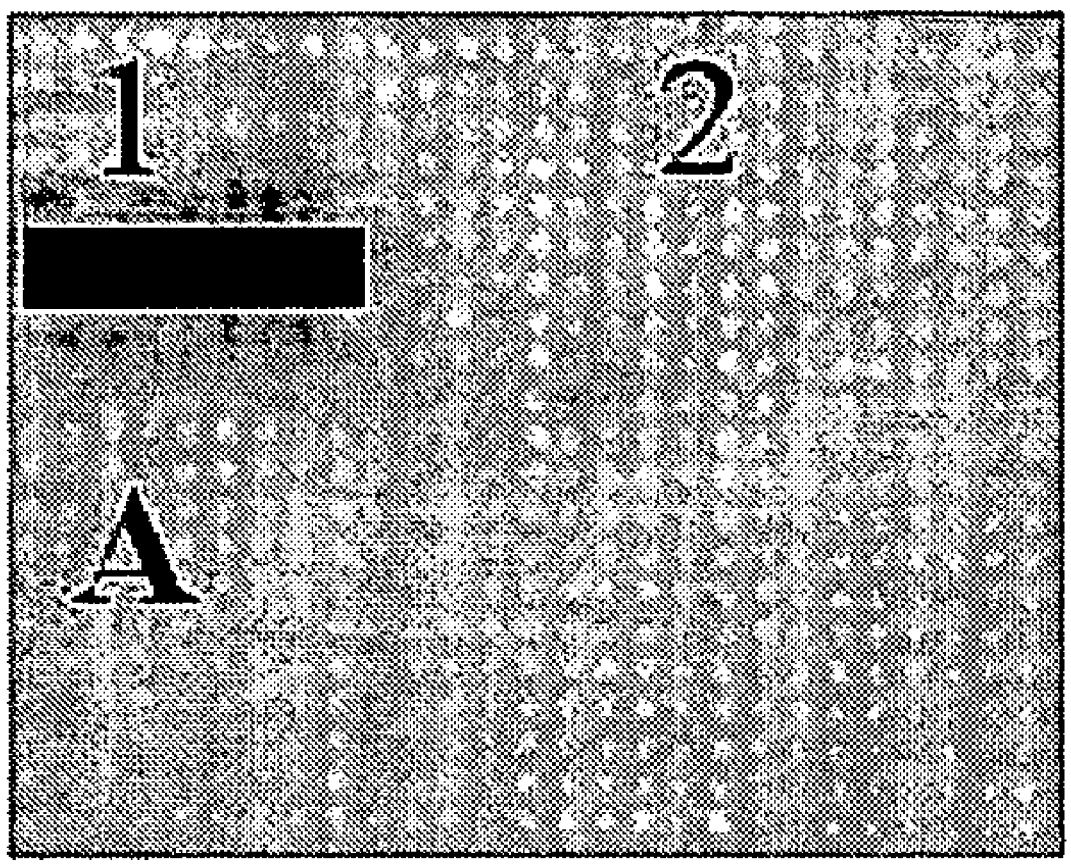
Figure 2B:
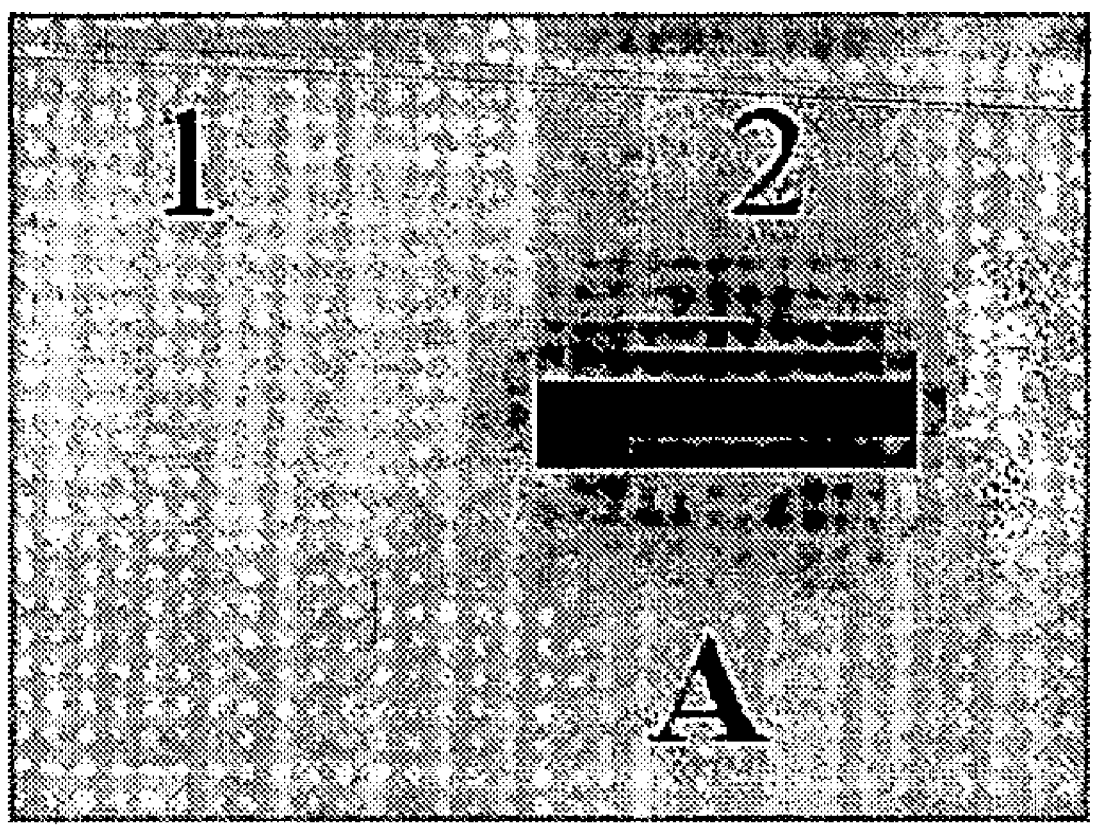
Figure 2C:
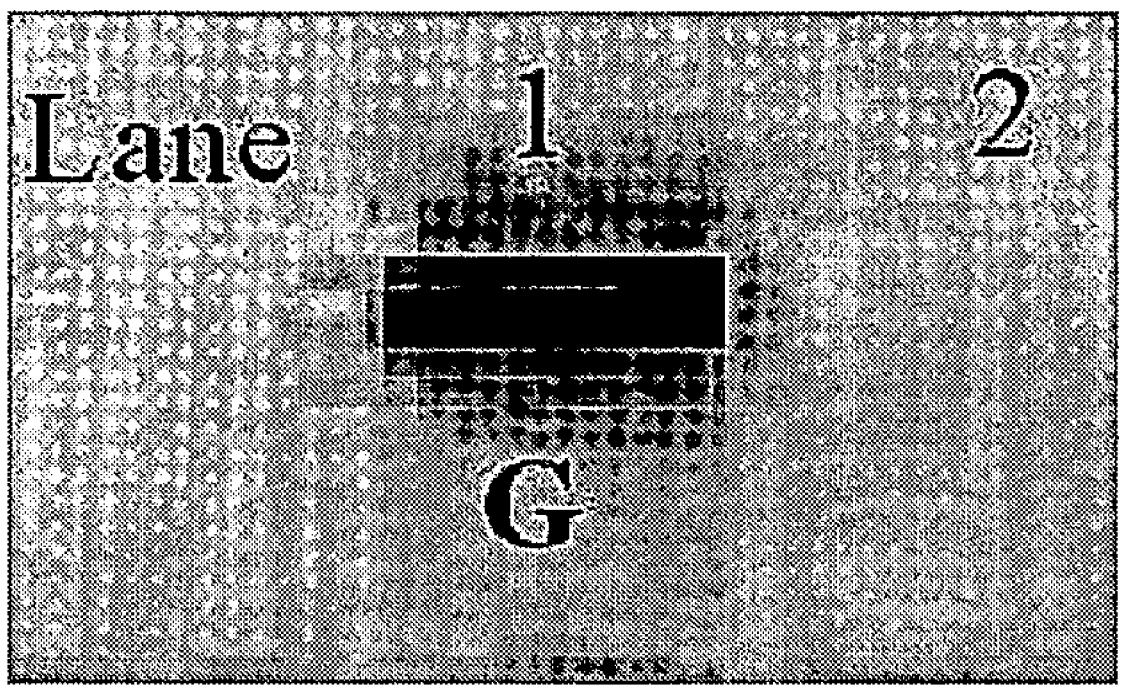
Figure 2D:
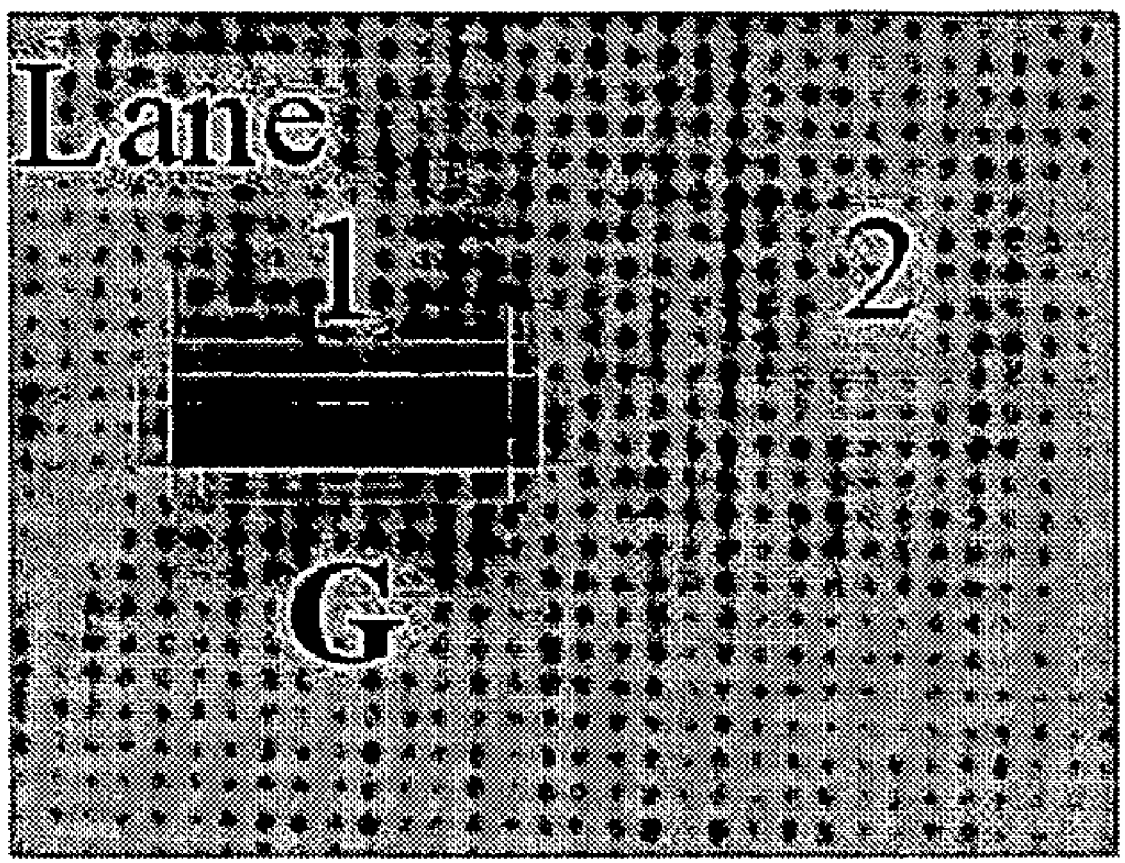

FIG. 2a Hydridization with allele specific primer having SEQ ID No.6 to show presence of A FIG. 2b Hydridization with allele specific primer having SEQ ID No.7 to show presence of A FIG. 2c Hydridization with allele specific primer having SEQ ID No.8 to show presence of G FIG. 2d Hydridization with allele specific primer having SEQ ID No.9 to show presence of G

SUMMARY OF THE INVENTION

The present invention discloses genotypes and haplotypes for ten polymorphic sites in the beta subtype 2, adrenergic receptor gene β2AR gene) in Indian population. Present invention relates to a method for predicting bronchodilatory response to a beta agonist (β agonist). The invention is of advantage to the Indian asthmatics in particular. This invention provides a method for detection of an allelic variant (genotype) in β2AR gene, which has been envisaged to be responsible for the key target for the β2-agonist used for bronchodilation. The invention is useful for developing a diagnostic kit for predicting individual drug response. Several missense polymorphisms within the coding block of the β2AR gene on chromosome 5q31 have been identified in the human population. The present invention also discloses the specific primers and probes for detecting the specific allelic variant in β2AR gene responsible for drug response.

DETAILED DESCRIPTION OF THE INVENTION

The β2AR is the key target for the β 2 agonist used for bronchodilation in asthma. Direct sequencing of coding region (only one exon) of this gene in the responder and non-responder patient samples led to the discovery of non-synonymous polymorphism associated with the drug response. In the individuals the codon AGA, which codes for amino acid arginine has changed to GGA, which codes for glycine. The nonsynonymous polymorphism if present in the homozygous state in the responder/non-responder individuals, could lead to the altered bronchodilation. Since nonsynonymous polymorphism in exonic region of the β2AR gene is associated with bronchodilation in asthma, this led to the discovery of nonsynonymous polymorphism in asthmatics associated with altered responsiveness. This polymorphism is found to predict altered invivo responsiveness. Further genotyping of several asthmatics (responders and non-responders) showed a significant association with altered response to β2 agonist. These results constitute the first demonstration of association of a single nucleotide polymorphism solely responsible for the altered responsiveness to β2 agonist.

The invention also provides oligonucleotide sequences (as listed in SEQ ID NO: 2, 3, 4, 5, 6, 7, 8 and 9) suitable for the detection of polymorphism in β2AR gene associated with the drug response.

A diagnostic kit predicting an individual's response to a beta agonist comprising one set of specific primers or probes along with the required buffers and accessories suitable for identification of polymorphism in β2AR gene to establish an individual's response towards β2 agonist is included in the invention.

Accordingly, the main embodiment of the present invention relates to a method for predicting and detecting bronchodilatory response to a β2 agonist in a subject suffering from asthma, said method comprising the steps of:

(a) administering the subject with pharmacologically active dose of known and fast acting β2 agonist through appropriate route,
(b) identifying and categorizing phenotypically good responders and poor responders suffering from asthma to the β2 agonist,
(c) isolating genomic DNA from the blood samples of the responders, non-responders suffering from asthma and normal individuals,
(d) designing and synthesizing oligonucleotide primers having SEQ ID Nos.2 and 3 capable of amplifying the coding region of β2AR gene or locus associated with asthma,
(e) amplifying the genomic DNA of the phenotypically categorized responders and non-responders asthmatic patients using SEQ ID Nos. 2 and 3,
(f) sequencing the amplified PCR product obtained in step (e) and identifying the nonsynonymoues polymorphism or single nucleotide polymorphisms (SNPs) of the sequenced PCR product obtained from step (e) computationally by comparing with the known sequence of β2AR gene or locus to detect the specific β2AR allelic variants,
(g) designing oligonucleotide primers having SEQ ID Nos. 4 and 5 till the penultimate position of the nonsynonymous polymorphism or single nucleotide polymorphisms (SNPs) identified in step (f) and screening the responder and non-responder asthmatic individuals for polymorphism at position 46 (which is same as the base position of 857 as per the SEQ ID NO. 1 disclosed in the present invention) to detect the specific SNPs of β2AR locus or gene, said process comprising of following PCR conditions:
(i) denaturing the isolated DNA at temperature of 96° C. for 10 seconds,
(ii) annealing the primers of SEQ ID Nos. 4 & 5 to denatured DNA of step (i) at a temperature of 55° C. for 5 seconds, and
(iii) undertaking the extension of annealed DNA of step (ii) at a temperature of 60° C. for 30 seconds,
(h) validating the normal control individuals and asthmatics patients (comprising of responders and non-responders) obtained in step (g) for presence of SNPs or specific β2AR allelic variants using allele specific oligonucleotide primers having SEQ ID Nos. 6, 7, 8 and 9, wherein the said oligonucleotides primers specifically hybridize to a target SNPs or specific β2AR allelic variants wherein the target SNPs or specific β2AR allelic variants have substitution of nucleotide A to G (A→G) at the position 46 (which is same as the base position of 857 as per the SEQ ID NO. 1 disclosed in the present invention) of β2AR gene or locus in the asthmatic patients.

One more embodiment of the present invention relates to a method of detecting and predicting specific allelic variants or Single nucleotide polymorphisms (SNPs) of β2AR gene in a subject suffering from asthma, said method comprising the steps of:

a. administering the subject with pharmacologically active dose of known but fast acting β2 agonist through appropriate route,
b. identifying and categorizing phenotypically good responders and poor responders suffering from asthma to the β2 agonist,
c. isolating genomic DNA from the blood samples of the responders, non-responders suffering from asthma and normal individuals,
d. designing and synthesizing oligonucleotide primers having SEQ ID Nos.2 and 3 capable of amplifying the coding region of β2AR gene associated with asthma,
e. amplifying the genomic DNA of the phenotypically categorized responders and non-responders asthmatic patients using SEQ ID Nos. 2 and 3,
f. sequencing the amplified PCR product obtained in step (e) and identifying the nonsynonymoues polymorphism or SNPs from the sequenced PCR product obtained from step (e) computationally by comparing with the known sequence of β2AR gene or locus to detect the specific β2AR allelic variants,
g. designing oligonucleotide primers having SEQ ID Nos. 4 and 5 till the penultimate position of the nonsynonymous polymorphic allelic variants or the SNPs identified in step (f) and screening the β2AR gene or locus for responder and non-responder asthmatic individuals for polymorphism at position 46 (which is same as the base position of 857 as per the SEQ ID NO. 1 disclosed in the present invention) to detect the specific SNPs or allelic variants, said process comprising of following PCR conditions:
(i) denaturing the isolated DNA at temperature of 96° C. for 10 seconds,
(ii) annealing the primers of SEQ ID Nos. 4 and 5 to the denatured DNA of step (i) at a temperature of 55° C. for 5 seconds, and
(iii) undertaking the extension of annealed DNA of step at a temperature of 60° C. for 30 seconds, and
h. validating the normal control individuals and asthmatics patients (comprising of responders and non-responders) obtained in step (g) for presence of SNP's or specific allelic β2AR or locus variants using allele specific oligonucleotide primers having SEQ ID Nos. 6, 7, 8 and 9, wherein the target SNPs or specific β2AR allelic variants have substitution of nucleotide A to G (A→G) at positions 46 (which is same as the base position of 857 as per the SEQ ID NO. 1 disclosed in the present invention) of β2AR gene or locus in the asthmatic patients.

Yet another embodiment of the present invention relates to a method for preparing pharmacogenetic markers for detecting and predicting bronchodilatory response to β-agonist in a subject suffering from asthma, said method comprising the steps of:
(a) administering the subject with pharmacologically active dose of known and fast acting β2 agonist through appropriate route,
(b) identifying and categorizing phenotypically good responders and poor responders to the β2 agonist,
(c) isolating genomic DNA from the blood samples of the responders, non-responders suffering from asthma and normal individuals,
(d) designing and synthesizing oligonucleotide primers having SEQ ID No.2 and SEQ ID No.3 capable of amplifying the coding region of β2AR gene associated with asthma,
(e) amplifying the genomic DNA of the phenotypically categorized responders and non-responders asthmatic patients using SEQ ID Nos. 2 and 3,
(f) sequencing the amplified PCR product obtained in step (e) and identifying the nonsynonymoues polymorphism or SNPs of the sequenced PCR product obtained from step (e) computationally by comparing with the known sequence of β2AR gene or locus to detect the specific β2AR allelic variants associates with asthma,
(g) designing oligonucleotide primers having SEQ ID Nos. 4 and 5 till the penultimate position of the nonsynonymous polymorphic or SNPs identified in step (f) and screening the responder and non-responder asthmatic individuals for polymorphism at position 46 (which is same as the base position of 857 as per the SEQ ID NO. 1 disclosed in the present invention) to detect the specific SNPs of β2AR gene or locus, said process comprising of following PCR conditions:
  (i) denaturing the isolated DNA at temperature of 96° C. for 10 seconds,
  (ii) annealing the primers of SEQ ID No. 4 and 5 to the denatured DNA of step (i) at a temperature of 55° C. for 5 seconds, and
  (iii) undertaking the extension of annealed DNA of step at a temperature of 60° C. for 30 seconds, and
(h) validating the normal control individuals and asthmatics patients (comprising of responders and non-responders) obtained in step (g) for presence of SNP's or specific allelic β2AR or locus variants using allele specific oligonucleotide primers having SEQ ID Nos. 6, 7, 8 and 9, wherein the target SNPs or specific β2AR allelic variants have substitution of nucleotide A to G (A→G) at positions 46 (which is same as the base position of 857 as per the SEQ ID NO. 1 disclosed in the present invention) of β2AR gene or locus in the asthmatic patients and functions as the pharamcogenetic marker.

Another embodiment of the present invention relates to novel pharmacogenetic markers for detecting and predicting bronchodilatory response to β-agonist in a subject suffering from asthma, said markers consisting of:
a. oligonucleotide primers having SEQ ID No.2 and SEQ ID No.3.
b. oligonucleotide primers having SEQ ID Nos. 4 and 5.
c. oligonucleotide primers having SEQ ID Nos. 6, 7, 8 and 9.

One more embodiment of the present invention relates to a diagnostic kit for predicting and detecting bronchodilating response of asthmatic patients to a β2 agonist said kit comprising of:
a. a first set of oligonucleotide primers having SEQ ID Nos. 2 and 3 for amplification of the marker region of the β2AR gene,
b. a second set of primers having SEQ ID Nos. 4 and 5 for genotyping the nonsynonymous polymorphism or single nucleotide polymorphism (AGA to GGA) said process comprising of following PCR conditions:
  (i) denaturing the isolated DNA at temperature of 96° C. for 10 seconds,
  (ii) annealing the primers of SEQ ID No. 4 and 5 to the denatured DNA of step (i) at a temperature of 55° C. for 5 seconds, and
  (iii) undertaking the extension of annealed DNA of step at a temperature of 60° C. for 30 seconds, and
c. a third set of primers having SEQ ID Nos. 6, 7, 8 and 9 for validating the normal control individuals and asthmatics patients (comprising of responders and non-responders) for presence of SNP's or specific allelic β2AR or locus variants using allele, wherein the target SNPs or specific β2AR allelic variants have substitution of nucleotide A to G (A→G) at positions 46 (which is same as the base position of 857 as per the SEQ ID NO. 1 disclosed in the present invention) of β2AR gene or locus in the asthmatic patients and functions as the pharamcogenetic marker Another embodiment of the present invention relates to the subject wherein the subject is a human.

Yet another embodiment of the present invention relates to the β2-agonist wherein the β2-agonist is salbutamol.

Still another embodiment of the present invention relates to the pharmacologically active dose of β2 agonist, salbutamol, wherein the pharmacologically active dose of β2 agonist, salbutamol, is in the range of about 100 to 250 µg.

One more embodiment of the present invention relates to the pharmacologically active dose of β2 agonist, salbutamol, wherein the pharmacologically active dose of β2 agonist, salbutamol, is about 200 µg.

Another embodiment of the present invention relates to the delivery of β2 agonist, salbutamol, wherein the active dose of β2 agonist, salbutamol, is delivered through inhaler.

Still another embodiment of the present invention relates to the oligonucleotide primers wherein the oligonucleotide primers suitable for amplifying coding region of β2AR are selected from group consisting of:

(i)  5'TCTGGGTGCTTCTGTGTTTGTTTC3'  (SEQ ID No. 2 Forward Primer)

(ii) 5'ACGATGGCCAGGACGATGAGA3    (SEQ ID NO: 3 Reverse Primer)

One more embodiment of the present invention relates to the oligonucleotide primers wherein the oligonucleotide primers suitable for amplifying detected nonsynonymous polymorphims or SNPs are selected from group consisting of:

a. 5'GCC TTC TTG CTG GCA CCC AAT3' (SEQ ID NO: 4) Forward Primer b. 5'CGTGGTCCGGCGCATGGCTTC3'       (SEQ ID NO: 5) Reverse Primer Yet another embodiment of the present invention relates to the number of PCR cycles wherein the number of PCR is carried out are 37.

Another embodiment of the present invention relates to oligonucleotide primers wherein oligonucleotide primers are suitable for validating the SNPs or the allelic variants of β2AR gene or locus are selected from group consisting of:

| (i) | 5'GCACCCAATAGAAGCCATG3' | (SEQ ID NO: 6) Forward Primer |
|---|---|---|
| (ii) | 5'CATGGCTTCTATTGGGTG C3' | (SEQ ID NO: 7) Reverse Primer |
| (i) | 5'GCACCCAATGGAAGCCATG3' | (SEQ ID NO: 8) Forward Primer |
| (ii) | 5'CATGGCTTCCATTGGGTG C3' | (SEQ ID NO: 9) Reverse Primer |

Still another embodiment of the present invention relates to the length of the synthetic oligonucleotide primers wherein the length of the synthetic oligonucleotides primers and probes are in the range of 5 to 100 bases.

One more embodiment of the present invention relates to the length of the synthetic oligonucleotide primers and probes wherein the length of oligonucleotide primers and probes are in the range of 8 to 24 bases.

Yet another embodiment of the present invention relates to the genotype wherein genotype GG is associated with good responder and genotype AA is associated with poor responders to salbutamol.

Another embodiment of the present invention is useful for development of therapeutics suitable for non-responder asthmatics for inducing bronchodilation.

Still another embodiment of the present invention relates to the developed method wherein the developed method provides markers primers and probes for predicting and detecting single allelic variant for β2AR gene or locus in humans.

Yet another embodiment of the present invention relates to the phramacogenetic markers wherein the phramcogenetic markers are associated with single specific allele variant or single nucleotide polymorphism (SNP) of β2AR gene or locus.

One more embodiment of the present invention relates to nonsynonymous polymorphism or SNPs wherein the identified nonsynonymous polymorphism or SNPs or the specific single β2AR allelic variant function as a pharmacogenetic markers.

Another embodiment of the present invention relates to the markers wherein markers/oligonucleotide primers having SEQ ID Nos 2 and 3 are capable of amplifying the coding region of β2AR gene.

Still another embodiment of the present invention relates to the markers wherein markers/oligonucleotide primers having SEQ ID Nos 4 and 5 are capable of screening and identifying responders and non responder asthmatic individuals for polymorphism at position 46 (which is same as the base position of 857 as per the SEQ ID NO. 1 disclosed in the present invention) to detect specific SNPs of β2AR gene.

One more embodiment of the present invention relates to the markers wherein markers/oligonucleotide primers having SEQ ID Nos 6, 7, 8 and 9 are capable of validating the normal control individuals and asthmatics patients (comprising of responders and non-responders) for presence of SNP's or specific allelic β2AR or locus variants.

Another embodiment of the present invention relates to a kit wherein said kit is useful for identifying therapeutics suitable for non-responder asthmatics for inducing bronchodilation.

Yet another embodiment of the present invention relates to a kit wherein the kit method provides markers, primers and probes for predicting and detecting single allelic variant for β2AR locus in humans.

Still another embodiment of the present invention relates to a kit wherein the identified nonsynonymous polymorphism or SNPs or the specific single β2AR allelic variant function as a pharmacogenetic markers for β2AR locus.

Another embodiment of the present invention relates to a kit wherein the kit is single specific β2AR allelic variants or the SNPs or the nonsynonymous polymorphisms function as pharmacogenetic markers towards β2 agonist.

One more embodiment of the present invention relates to a kit which further comprises instructions for using the oligonucleotides and assigning the response type based on AA or GG genotypes of β2AR gene variants.

The following examples are given by way of illustration of the present invention and should not be construed to limit the scope of the present invention.

EXAMPLES

Example 1

Population Study: Measurement of Airway Reactivity by Inhaled β2 Agonist

As a first step to the present invention, applicants carried out the study by administering the patients with short-acting beta agonist e.g. salbutamol, which showing the various degree of responses, for making more descriptive study we classified the patients on the basis of their responses to salbutamol as Good responders and Poor responders. Salbutamol can be taken either orally or more commonly using an inhaler device. The inhaler ensures that very small amounts of medication are delivered directly into the lungs. The diagnosis of Asthma was made on the basis of positive history of signs and symptoms consistent with the disease and by the presence of reversible airway obstruction. All patients underwent routine laboratory diagnostics tests and pulmonary function test (PFT) to exclude other possible chest diseases. In the spirometry test, a minimum of three acceptable maneuvers were performed and the "best-test" curve was chosen ("Best-test" curve is defined as the test that meets the acceptability criteria laid down by American Thoracic Society and gives the largest sum of FVC and FEV1). The patients who showed signs of obstruction in the airways, were given 200 micrograms of salbutamol (beta 2 adrenergic agonist) and the test was repeated after 20 minutes. This was done to assess the degree of reversibility of obstruction of the airways. The same procedure was repeated 2-3 times at intervals of more than two weeks, and the best value of % age change in FEV1 was chosen to classify the asthmatics as good, poor or non-responder to salbutamol.

Example 2

II. Identification of Polymorphisms in β2AR Gene:

The inventors have identified ten polymorphic sites in the Indian population in a contiguous region of the 5' upstream and coding sequence of the β2AR gene in Indian population (Table 2). This finding is different from the findings of Drysdale et al (2000) wherein thirteen polymorphic sites have been reported.

Seven haplotype pairs shown in Table 3 were estimated from the unphased genotypes using extension of Clark's algorithm (Clark, 1990), in which haplotypes are assigned directly from individuals who are homozygous at all sites or heterozygous at no more than one of the variable sites.

Example 3

III. Single Polymorphism of the Invention as a Dictator of Drug Response:

The applicants carried out the PCR amplification of exonic region of the human β2 A R gene using oligonucleotide primers. These primers were designed in accordance with the human β2 A R gene sequence submitted by DOE Joint Genome Institute and Stanford Human Genome Center (6 Oct. 1999) (GenBank accession number-AC011354). The sequencing of the purified PCR product revealed homozygous nonsynonymous polymorphism in exonic region of the human β2AR gene associated with bronchodilation.

The present invention provides a sequence for the allelic variants of human β2AR gene comprising nonsynonymous polymorphism in exonic region of the human β2AR gene sequence in the database (GenBank Accession No.-AC011354) associated with drug response.

TABLE 1

| Site of change | Base change | Amino-acid alteration |
|---|---|---|
| 857 | A → G | Arginine to Glycine |

The sites of changes are in accordance with the PCR Product Sequence obtained using primers (SEQ ID 2 and 3) flanking exonic region of the human β2AR gene (GenBank accession number-AC011354).

The substitution A→G changes amino acid arginine to glycine which consequently leads to the nucleotide sequence of the allelic variant of exonic region of the human β2AR gene. PCR Product Sequence containing the nonsynonymous polymorphism is obtained using primers SEQ ID 2 and 3 flanking nonsynonymous polymorphism in exonic region of the human β2AR gene of SEQ ID 1.

The polymorphic site is at nucleotide position 857 in the above sequence (A*) corresponds to nucleotide position 46 from the database (GenBank Accession No.-AC011354). The primers are used to detect polymorphism at position 857 according to the PCR product obtained using primers (SEQ ID 2 and 3) flanking exonic region of the human β2AR gene (Table 1).

Example 4

IV. Association Analysis with the Drug Response:

The inventors herein have discovered that a patient's bronchodilating response to salbutamol in Indian population may be predicted with high confidence by genotyping only one polymorphic site in the β2AR gene at nucleotide position 46. Further genotyping of several asthmatics (responders and non-responders) showed a significant association with altered response to β agonist. These results constitute the first demonstration of association of a single polymorphism responsible for the altered responsiveness to β agonist. Homozygous Arg16 and homozygous Gly16 showed association with poor and good response in Indian population (FIG. 1d). Furthermore, the very small number of homozygous Arg16 asthmatics who had a positive bronchodilator response and Gly16 asthmatics who had a negative bronchodilator response, the potential confoundment of race, and the use of mild pediatric asthmatics, makes the others (Martinez et al., 1997) study incomparable to the inventor's study described herein which utilized the Indian asthmatics in particular, a greater number of asthmatics and adult Indian subjects having a range of asthma severity. The applicants could not find any SNP in β2AR gene associated with asthma in Indian population.

Example 5

V) Diagnostic Kits:

The invention further provides a diagnostic kit for predicting an individual's response to a beta agonist comprising:
PCR amplification primers of SEQ ID 2 and 3,
Snapshot primer of SEQ ID No. 4 or 5,
At least one allele-specific oligonucleotide selected from oligonucleotides of SEQ ID Nos. 6, 7, 8, and 9.
Appropriate buffers for PCR or hybridization reactions.

The allele-specific oligonucleotides may alternatively be provided as immobilized to a substrate, which can be used to detect polymorphism in β2AR gene.

Optional additional components of the kit include, for example, restriction enzymes, polymerase, the substrate nucleoside triphosphates, means used to label (for example, an avidin enzyme conjugate and enzyme substrate and chromogen if the label is biotin).

Example 6

Measurement of Airway Reactivity by Inhaled β2 Agonist

The diagnosis of Asthma was made on the basis of positive history of signs and symptoms consistent with the disease and by the presence of reversible airway obstruction. All patients underwent routine laboratory diagnostics tests and pulmonary function test (PFT) to exclude other possible chest diseases. In the spirometry test, a minimum of three acceptable maneuvers were performed and the "best-test" curve was chosen ("Best-test" curve is defined as the test that meets the acceptability criteria laid down by American Thoracic Society and gives the largest sum of FVC and FEV1). The patient who showed signs of obstruction in the airways were given 200 micrograms of salbutamol (β 2 agonist) and the test was repeated after 20 minutes. This was done to assess the degree of reversibility of obstruction of the airways. The same procedure was repeated 2-3 times at intervals of more than two weeks, and the best value of % age change in FEV1 was chosen to classify the asthmatics as good, poor or non-responder to salbutamol.

Example 7

Identification of Polymorphisms in β2AR Gene:

The inventors identified ten polymorphic sites in a contiguous region of the 5' upstream and coding sequence of the β2AR gene in Indian population (Table2). It illustrates examination of the ten polymorphic sites from 1581 base pairs upstream of the ATG start site to about 750 base pairs downstream of the ATG start site. Thirteen polymorphic sites found in humans by Drysdale et al (2000) is different from our finding of only ten polymorphic sites in Indian population. Seven haplotype pairs shown in Table 3 were estimated from the unphased genotypes using extension of Clark's algorithm (Clark, 1990), in which haplotypes are assigned directly from individuals who are homozygous at all sites or heterozygous at no more than one of the variable sites.

Overlapping parts of the β2AR gene were amplified from genomic DNA from the asthma patients and normal Indian individuals using the following PCR primers, with the indicated positions corresponding to GeneBank Accession No. AC011354.

Part 1

Positions of the primers are based on the first nucleotide of the start codon being +1.
Forward Primer: nt −1472 to −1448
Reverse Primer: complement of nt −530 to −548
942 nt product (−1472 to −530)

Part 2
Forward Primer (SEQ ID 2): nt −811 to −787
Reverse Primer (SEQ ID 3): complement of nt +143 to +122
954 nt product (−811 to +143)

Part 3
Forward Primer (5): nt +126 to +148
Reverse Primer (6): complement of nt +721 to +699
595 nt product (+721 to +126)

TABLE 2

Polymorphisms identified in the β2AR gene in Indian population

Nucleotide number is based on the first nucleotide of the start codon being +1

| Position | Allele | Allele |
|---|---|---|
| −1023 | G | A |
| −654 | G | A |
| −468 | G | C |
| −367 | C | T |
| −47 | C | T |
| −20 | T | C |
| 46 | A | G |
| 79 | C | G |
| 252 | G | A |
| 523 | C | A |

TABLE 3

Seven haplotype pairs shown here in the table were estimated from the unphased genotypes using extension of Clark's algorithm (Clark, 1990), in which haplotypes are assigned directly from individuals who are homozygous at all sites or heterozygous at no more than one of the variable sites.

| | −1023 | −654 | −468 | −367 | −47 | −20 | 46 | 79 | 252 | 523 |
|---|---|---|---|---|---|---|---|---|---|---|
| 1. | A | G | G | C | C | C | G | G | G | C |
| 2. | G | A | C | T | T | T | A | C | G | C |
| 3. | G | A | C | T | T | T | G | C | G | C |
| 4. | G | G | C | T | T | T | G | C | A | A |
| 5. | G | A | C | T | T | T | A | C | A | A |
| 6. | G | G | C | T | T | T | G | C | A | C |
| 7. | G | G | C | T | T | T | G | C | G | C |

Example 8

Identification of Nonsynonymous Polymorphism in β2AR Gene:

This example describes the identification of nonsynonymous polymorphism in exonic region of β2AR gene by PCR and sequencing, using certain oligonucleotide primers according to the invention.

Genomic DNA was isolated from peripheral blood using salt-precipitation method (Miller et al., 1988). The concentration of the DNA was determined by measuring the absorbance of the sample, at a wavelength of 260 nm. The DNA from asthmatics was then amplified by polymerase chain reaction by using the oligonucleotide primer 2 and 3 (SEQ ID 2 and 3). Each 50 μl PCR reaction contained 200 ng DNA, 20 pmol each of oligonucleotide primer 2 and 3 (SEQ ID 2 and 3), 1.8 units Taq Polymerase (Bangalore Genei), and 200 mM deoxyribonucleoside triphosphate (dNTP) in a 10×PCR buffer (containing 100 mM Tris (pH 9.0), 500 mM KCl, and 0.1% Gelatin).

The samples were denatured at 94° C. for 5 min followed by 37 cycles of denaturation 94° C., 45 sec), annealing (56° C., 1min), extension (72° C., 1.2 min) and a final extension of 10 min at 72° C. in a Perkin Elmer Gene Amp PCR System 9600. This reaction produced a DNA fragment of 954 bp. PCR products were purified by Poly Ethylene Glycol/Sodium acetate solution (containing PEG 8000, 1M Magnesium chloride and 3M anhydrous Sodium acetate, pH-4.8) and both the strands of the PCR product were directly sequenced using dye terminator chemistry on an ABI Prism 3100 automated DNA sequencer. The PCR product was shown to be identical to the exon of the β2AR gene sequence in the database (Accession Number-AL022326). Sequences were aligned with the corresponding wild-type sequences using the Factura and Sequence Navigator software programs Example 9

Screening Polymorphism in the Population:

This example describes a primer extension reaction used to screen single nucleotide variants. The DNA samples from several asthmatics (responders/non-responders) and several normal subjects were amplified by PCR and the PCR products were purified as described in example 2. The primer extension reaction was performed on the purified PCR products using oligonucleotide primer and SNaPshot ddNTP primer extension kit (PE Biosystems). The snapshot technique is extensively used in the molecular studies and is useful in exact base identity determination of a polymorphic locus. Although, the basic methodology followed for all snapshot protocols is same in all studies. But the each snapshot protocol is unique in itself. This is because each protocol is locus specific. Therefore, a specific working protocol has to be developed and invented for identification of specific locus. In other words the reaction and PCR conditions developed using the snapshot technique in the present study is different from any other snapshot technique used for any other disease locus. This means that the novel specific protocol of snapshot technique as given in the present invention has been established for this very specific locus i.e for β2AR locus. This protocol will only work if only these specific designed and developed primers having SEQ ID No. 4 and SEQ ID No.5 are used. The oligonucleotide primer was designed till the penultimate position of mutation and the primer is extended by one ddNTP, which is in accordance with the variant allele present. The reaction was performed for 30 cycles of denaturation (96° C., 10 sec), annealing (55° C., 5 sec) and extension (60° C., 30 sec) in a Perkin Elmer GeneAmp PCR System 9600 using primers having SEQ ID No. 4 and SEQ ID No.5. The primer extension products were treated with calf intestine alkaline phosphatase (New England Biolabs) for removing unincorporated dideoxynucleotides. The products were run on an ABI Prism 3100 automated DNA sequencer. Depending on the colour of the fluorescently labeled dideoxynucleotide incorporated, the wild type and polymorphic alleles of the β2AR gene were detected.

Example 10

Nucleotide Sequence of Allelic Variants of β2 A R Gene:
The nucleotide sequence of the allelic variant of β2AR gene derived using the method as described in example 2— be predicted with high confidence by genotyping only one polymorphic site in the β2AR gene at nucleotide position 46. Further genotyping of several asthmatics (responders and non-responders) showed a significant association with altered response to β2 agonist. These results constitute the first demonstration of association of a single polymorphism solely responsible for the altered responsiveness to β2 agonist. Homozygous Arg16 and homozygous Gly16 showed association with poor and good response in Indian population (FIG: 1d). Furthermore, the very small number of homozygous Arg16 asthmatics who had a positive bronchodilator

```
5'GTT CGG AGT ACC CAG ATG GAG ACA TCC GTG TCT GTG TCG CTC    (SEQ ID 1)

TGG ATG CCT CCA AGC CAG CGT GTG TTT ACT TTC TGT GTG TGT CAC

CAT GTC TTT GTG CTT CTG GGT GCT TCT GTG TTT GTT TCT GGC CGC

GTT TCT GTG TTG GAC AGG GGT GAC TTT GTG CCG GAT GGC TTC TGT

GTG AGA GCG CGC GCG AGT GTG CAT GTC GGT GAG CTG GGA GGG

TGT GTC TCA GTG TCT ATG GCT GTG GTT CGG TAT AAG TCT GAG CAT

GTC TGC CAG GGT GTA TTT GTG CCT GTA TGT GCG TGC CTC GGT GGG

CAC TCT CGT TTC CTT CCG AAT GTG GGG CAG TGC CGG TGT GCT GCC

CTC TGC CTT GAG ACC TCA AGC CGC GCA GGC GCC CAG GGC AGG

CAG GTA GCG GCC ACA GAA GAG CCA AAA GCT CCC GGG TTG GCT

GGT AAG GAC ACC ACC TCC AGC TTT AGC CCT CTG GGG CCA GCC

AGG GTA GCC GGG AAG CAG TGG TGG CCC GCC CTC CAG GGA GCA

GTT GGG CCC CGC CCG GGC CAG CCC CAG GAG AAG GAG GGC GAG

GGG AGG GGA GGG AAA GGG GAG GAG TGC CTC GCC CCT TCG CGG

CTG CCG GCG TGC CAT TGG CCG AAA GTT CCC GTA CGT CAC GGC

GAG GGC AGT TCC CCT AAA GTC CTG TGC ACA TAA CGG GCA GAA CGC

ACT GCG AAG CGG CTT CTT CAG AGC ACG GGC TGG AAC TGG CAG

GCA CCG CGA GCC CCT AGC ACC CGA CAA GCT GAG TGT GCA GGA

CGA GTC CCC ACC ACA CCC ACA CCA CAG CCG CTG AAT GAG GCT TCC

AGG CGT CCG CTC GCG GCC CGC AGA GCC CCG CCG TGG GTC CGC

CCG CTG AGG CGC CCC CAG CCA G TG CGC TTA CCT GCC AGA CTG

CGC GCC ATG GGG CAA CCC GGG AAC GGC AGC GCC TTC TTG CTG

GCA CCC AAT A*GA AGC CAT GCG CCG GAC CAC GAC GTC ACG CAG

CAA AGG GAC GAG GTG TGG GTG GTG GGC ATG GGC ATC GTC ATG

TCT CTC ATC GTC CTG GCC ATC GTG TTT GGC AAT GTG CTG GTC ATC

ACA GCC ATT GCC AAG T TC GAG CGT CTG CAG ACG GTC ACC AAC TAC

TTC ATC ACT TCA CTG GCC TGT GCT GAT CTG GTC3'
```

Example 11

The Association of Non-synonymous Polymorphism with Drug Response
The non-synonymous SNP or polymorphism are defined as "when the altered code doesn't correspond to the same amino acid as the wild type sequence i.e these are substitutions in coding region that result in a different amino acid".
The inventors herein have discovered that a patient's bronchodilating response to salbutamol in Indian population may response and Gly16 asthmatics who had a negative bronchodilator response, the potential confoundment of race, and the use of mild pediatric asthmatics, makes the others (Martinez et al., 1997) study incomparable to the inventor's study described herein which utilized the Indian asthmatics in particular, a greater number of asthmatics and adult Indian subjects having a range of asthma severity. The applicants could not find any SNP in β2AR gene associated with asthma in Indian population.

A patient having AA genotype is expected to be a poor responder with probability 0.76 and one with GG genotype is expected to be a good responder with probability 0.72.

The responder status to salbutamol treatment and genotype at β2AR gene of a asthmatic patient are strongly associated in the Indian population ($\chi 2=11.28$, df=2, p=0.004).

Example 12

For validatation of polymorphism at nucleotide position 46, a sequence specific oligonucleotide (SSO) hybridation experiments were set up. The experiments were based on the amplification of the region of interest by polymerase chain reaction (PCR) followed by blotting of the PCR products on to a nylon membrane and subsequent hybridization with the radiolabelled primers of SEQ ID No.6, 7, 8 and 9. The DNA from asthmatics was amplified by polymerase chain reaction using the oligonucleotide primer 2 and 3 (SEQ ID 2 and 3). Each 50 µl PCR reactions contained 200 ng DNA, 20 pmol each of oligonucleotide primer 2 and 3 (SEQ ID No. 2 and 3), 1.8 units Taq Polymerase (Bangalore Genei), and 200 mM deoxyribonucleoside triphosphate (dNTP) in a 10×PCR buffer (containing 100 mM Tris (pH 9.0), 500 mM KCl, and 0.1% Gelatin).

1 microlitre each of the PCR products generated as above were electrophoresed on a 1% agarose gel and transferred onto the nylon membrane and hybridized in 6×SSPE (NaCl 0.9M; NaH2PO4 70 mM; EDTA 6 mM), 0.5% sodium dodecyl sulphate (SDS), 5× Denhardt's, and 100 µg/ml salmon sperm DNA with the oligonucleotide primers specific for nucleotide position 46 (the radiolabelled primers of SEQ ID No. 6, 7, 8 and 9). Hybridization were carried out under stringent conditions at the melting temperature of each oligonucleotide which was determined as per standard protocol. The filters were washed twice at room temperature in 2×SSPE, 0.1% SDS for 10 min, once 2° C. above the melting temperature in 6×SSPE, 1% SDS for 10 min and then exposed to autoradiography. The exposed radiographs were analysed for the hybridized spots resulting from hybridization of the PCR products of the sequence containing the SNP at position 46 with the radiolabelled allele specific primers of SEQ ID no.6, 7, 8 and 9. The results of the allele specific primers of SEQ ID No. 6, 7, 8 and 9 are shown in FIGS. 2a, 2b, 2c, 2d respectively.

In FIGS. 2a and 2b, out of the two lanes, one lane in each figure, showed a hybridized spot with the allele specific primer of SEQ ID No. 6 and 7, confirming presence of the allele A where as in FIG. 2c and FIG. 2d, the hybridized spots with allele specific primers of SEQ ID No. 8 and 9 confirmed the presence of the allele G at the 46 nucleotide position.

REFERENCES

1. Bjermer, L., Diamant, Z. (2002). The use of leukotriene receptor antagonists (LTRAS) as complementary therapy in asthma. Monaldi Arch Chest Dis. 57(1):76-83.
2. Chabra S. K. (1998). Epidemiology of childhood asthma. Ind. J. of Chest Disease & Allied Sci. 40: 179-93.
3. Clark, A. G., Mol Bio Evol 7, 111-122, 1990.
4. Cockcroft, D. W. and Swystun, V. A.(1996). Functional antagonism: tolerance produced by inhaled beta 2 agonist. Thorax 51, 1051-1056.
5. Dennis S. M., Sharp S. J., Vickers M. R., et al. (2000). Regular inhaled salbutamol and asthma control: the TRUST randomized trial. Therapy Working Group of the National Asthma Task Force and the MRC General Practice Research Framework. Lancet 355:1675-9
6. Dewar, Wheatley, Venn, Morrison, Britton & Hall (1998). Beta2-adrenoceptor polymorphisms are in linkage disequilibrium, but are not associated with asthma in an adult population. Clinical & Experimental Allergy, 28 (4):442-448.
7. Dewar, J. C., Wilkinson, J., Wheatley, A., N. Thomas, S. (1997). The glutamine 27 beta2-adrenoceptor polymorphism is associated with elevated IgE levels in asthmatic families. Journal of Allergy and Clinical Immunology. 100 (2): 261-265.
8. Drysdale, Connie M., Judson, Richard S., Liggett, Stephen B., Nandabalan, K., Stack, Catherine B., Stephens, J. Claiborne (2002). Association of beta2-adrenergic receptor haplotypes with drug response.
9. Eh, W., Walters, J., Gibson, Mdp (2003). Inhaled long acting beta agonists for stable chronic asthma. Cochrane Database Syst Rev.; 4:CD001385.
10. Green, S. A. (1994). Amino-Terminal Polymorphisms of the Human B2-Adrenergic Receptor Impart Distinct Agonist-Promoted Regulatory Properties. Biochemistry, Vol. 33, P. 9414-9419.
11. Green, S. A., Turki, J., Bejarano, P., Hall, I. P., and Liggett, S. B. (1995). Influence of beta 2-adrenergic receptor genotypes on signal transduction in human airway smooth muscle cells. Am. J. Respir. Cell Mol. Biol. 13: 25-33.
12. Hoit, B. D., Suresh, D. P., Craft, L., Walsh, R. A., Liggett S. B. (2000). Beta2-adrenergic receptor polymorphisms at amino acid 16 differentially influence agonist-stimulated blood pressure and peripheral blood flow in normal individuals. Am Heart J. 139(3):537-42.
13. Jeffrey, M. Drazen, Edwin K. Silverman and Tak H. Lee (2000). Heterogeneity of therapeutic responses in asthma. British Medical Bulletin 56:1054-1070.
14. Johnson, M. (1998) The beta-adrenoceptor. Am J Respir Crit Care Med. 158(5 Pt 3):S146.
15. Kobilka, B. K., Dixon, R. A., Frielle, H. G., Dohlman, M. A., Bolanowski, I. and Sigal I. S. (1987). cDNA for the human beta2-adrenergic receptor: a protein with multiple spanning domains and encoded by a gene whose chromosomal location is shared with that of a receptor for platelet growth factor. Proc. Natl. Acad. Sci 84:46-50.
16. Large, V., Hellström, L., Reynisdottir, S., Lönnqvist, F., Eriksson, P., Lannfelt, L and Amer, P (1997). Human Beta-2 Adrenoceptor Gene Polymorphisms Are Highly Frequent in Obesity and Associate with Altered Adipocyte Beta-2 Adrenoceptor Function. J. Clin. Invest. 100: 3005-3013.
17. Liggett, S. B., Wagoner, L E., Craft, L. L., Hornung, R. W., Hoit, B. D., McIntosh, T. C. and Walsh, R. A (1998). The Ile164

$_2$-Adrenergic Receptor Polymorphism Adversely Affects the Outcome of Congestive Heart Failure. J. Clin. Invest. 102:1534-1539. Lipworth, B. J., Hall, I. P., Aziz, I., Tan, K. S. and Wheatley, A. (1999). Beta2-Adrenoceptor polymorphism and bronchoprotective sensitivity with regular short- and long-acting beta2-agonist therapy. Clinical Science 96: 253-259.

18. Martin, R. J. (2003).Considering therapeutic options in the real world. J Allergy Clin Immunol. 112(5 Suppl): S112-115.
19. Martinez, F. D., Graves, P. E., Baldini, M., Solomon, S. and Erickson, R. (1997). Association between Genetic Polymorphisms of the beta2-Adrenoceptor and Response to Albuterol in Children with and without a History of Wheezing. J. Clin. Invest. 100:3184-3188.
20. National Asthma Education and Prevention Program (1997) Expert Panel Report II, Guidelines for the Diagnosis and Management of Asthma, National Institutes of Health Publication 9724051, Bethesda, Md.
21. Ohe, M., Munakata, M., Hizawa, N., Itoh, A., Doi, I., Yamaguchi, E., Homma, Y and Kawakami, Y (1995). Beta 2 adrenergic receptor gene restriction fragment length polymorphism and bronchial asthma. Thorax 50: 353-359.
22. O'Connor B. J., Aikman S. L., and Barnes P. J. (1992). Tolerance to the nonbronchodilator effects of inhaled beta 2-agonists in asthma. N Engl J Med 327:1204-8
23. Reihsaus, E., Innis, M., MacIntyre, N and Liggett, S. B. (1993) Mutations in the gene encoding for the beta 2-adrenergic receptor in normal and asthmatic subjects. Am J Respir Cell Mol Biol. 8(3):334-339.
24. Scott M. G. H., Swan C., Wheatley A. P., and Hall I. P. (1999). Identification of novel polymorphisms within the promoter region of the human $\beta_2$ adrenergic receptor gene. Br J Pharmacol 126: 841-844.
25. Suki B., Frey (2003). Temporal dynamics of recurrent airway symptoms and cellular random walk. U. J Appl Physiol. 95(5):2122-21227.
26. Settipane, R. A. (2003). Defining the effects of an inhaled corticosteroid and long-acting beta-agonist on therapeutic targets. Allergy Asthma Proc. March-April; 24(2):85-89.
27. 28. Sakane, N., Yoshida, T., Umekawa, T., Kogure, A., Kondo, M. (1999). $\beta_2$-adrenoceptor gene polymorphism and obesity. Lancet 353 (9168):1976.
28. Turki, J., John N. Lorenz, Stuart A. Green, Elizabeth T. Donnelly, Marie Jacinto, and Stephen B. Liggett. (1996). Myocardial signaling defects and impaired cardiac function of a human beta2-adrenergic receptor polymorphism expressed in transgenic mice. PNAS 93: 10483-10488.
29. Turki J, Pak J, Green S A, Martin R J, Liggett S B (1995). Genetic polymorphisms of the beta 2-adrenergic receptor in nocturnal and nonnocturnal asthma. Evidence that Gly16 correlates with the nocturnal phenotype. J Clin Invest. 95(4):1635-1641.
30. Tan, S., Hall, I. P., Dewar, J., Dow, E., Lipworth, B. (1997). Association between $\beta_2$-adrenoceptor polymorphism and susceptibility to bronchodilator desensitisation in moderately severe stable asthmatics. Lancet 350 (9083): 995.
31. Xu, B. Y., Huang, D., Pirskanen, R & Lefvert, A. K. (2000). Beta2-adrenergic receptor gene polymorphisms in myasthenia gravis (MG). Clinical & Experimental Immunology 119 (1) Page 156.

We claim:

1. A method for detecting a single nucleotide polymorphism A46G in a β2AR gene in a human subject suffering from asthma and identifying the human subject as a good responder to a short acting β2 agonist based on the genotype at nucleotide position 46 of the beta 2AR gene said method comprising the steps of:
   (a) isolating genomic DNA from the human subject,
   (b) amplifying the genomic DNA using oligonucleotide PCR primers set forth in SEQ ID NOS. 2 and 3,
   (c) sequencing the PCR amplified genomic DNA obtained in step (b)
   (d) detecting the single nucleotide polymorphism A46G in the sequenced PCR amplified genomic DNA from step (c),
   (e) identifying specific β2AR genotypes AA, AG and GG, and
   (f) based on the information from step (e), identifying the human subject to be a good responder to the short acting β2 agonist if said subject has GG genotype and a poor responder to the short acting β2 agonist if said subject has the AA genotype.

2. A method as claimed in claim 1, wherein the short acting β2-agonist is salbutamol.

3. A method as claimed in claim 2, wherein the pharmacologically active dose of β2-agonist, salbutamol, is in the range of 100 to 250 μg.

4. The method of claim 1 wherein said detecting comprises amplification and/or primer extension with primers selected from the group consisting of:
   (a) oligonucleotide primers having SEQ ID Nos. 2 and 3,
   (b) oligonucleotide primers having SEQ ID Nos. 4 and 5, and
   (c) oligonucleotide primers having SEQ ID Nos. 6,7,8 and 9.

5. The method of claim 4, wherein said detecting comprises:
   (a) denaturing the isolated DNA at temperature of 96° C. for 10 seconds,
   (b) annealing the primers of SEQ ID No. 4 and 5 to denatured DNA of step (a) at a temperature of 55° C. for 5 seconds, and
   (c) undertaking the extension of annealed DNA of step (b) at a temperature of 60° C. for 30 seconds.

6. The method of claim 5, further comprising amplification and/or primer extension from primers having SEQ ID Nos. 6, 7, 8 and 9.

* * * * *

SEQUENCE LISTING

```
<160> NUMBER OF SEQ ID NOS: 9

<210> SEQ ID NO 1
<211> LENGTH: 1155
<212> TYPE: DNA
<213> ORGANISM: Homo sapiens

<400> SEQUENCE: 1
gttcggagta cccagatgga gacatccgtg tctgtgtcgc tctggatgcc tccaagccag      60
cgtgtgttta ctttctgtgt gtgtcaccat gtctttgtgc ttctgggtgc ttctgtgttt     120
gtttctggcc gcgtttctgt gttggacagg ggtgactttg tgccggatgg cttctgtgtg     180
agagcgcgcg cgagtgtgca tgtcggtgag ctgggagggt gtgtctcagt gtctatggct     240
gtggttcggt ataagtctga gcatgtctgc cagggtgtat ttgtgcctgt atgtgcgtgc     300
ctcggtgggc actctcgttt ccttccgaat gtggggcagt gccggtgtgc tgccctctgc     360
cttgagacct caagccgcgc aggcgcccag ggcaggcagg tagcggccac agaagagcca     420
aaagctcccg ggttggctgg taaggacacc acctccagct ttagccctct ggggccagcc     480
agggtagccg ggaagcagtg gtggcccgcc ctccagggag cagttgggcc ccgcccgggc     540
cagccccagg agaaggaggg cgaggggagg ggaggggaaag gggaggagtg cctcgcccct     600
tcgcggctgc cggcgtgcca ttggccgaaa gttcccgtac gtcacggcga gggcagttcc     660
cctaaagtcc tgtgcacata acgggcagaa cgcactgcga agcggcttct tcagagcacg     720
ggctggaact ggcaggcacc gcgagcccct agcacccgac aagctgagtg tgcaggacga     780
gtccccacca cacccacacc acagccgctg aatgaggctt ccaggcgtcc gctcgcggcc     840
cgcagagccc cgccgtgggt ccgcccgctg aggcgccccc agccagtgcg cttacctgcc     900
agactgcgcg ccatggggca acccgggaac ggcagcgcct tcttgctggc acccaataga     960
agccatgcgc cggaccacga cgtcacgcag caaagggacg aggtgtgggt ggtgggcatg    1020
```

```
ggcatcgtca tgtctctcat cgtcctggcc atcgtgtttg gcaatgtgct ggtcatcaca    1080
gccattgcca agttcgagcg tctgcagacg gtcaccaact acttcatcac ttcactggcc    1140
tgtgctgatc tggtc                                                     1155
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2

```
tctgggtgct tctgtgtttg tttc                                             24
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3

```
acgatggcca ggacgatgag a                                                21
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4

```
gcctccttgc tggcacccaa t                                                21
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5

```
cgtggtccgg cgcatggctt c                                                21
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6

```
gcacccaata gaagccatg                                                   19
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 7

```
catggcttct attgggtgc                                                   19
```

<210> SEQ ID NO 8

```
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
gcacccaatg gaagccatg                                             19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
catggcttcc attgggtgc                                             19
```